United States Patent
Verhagen et al.

(10) Patent No.: US 10,292,766 B2
(45) Date of Patent: May 21, 2019

(54) DEVICE FOR CUTTING HAIR

(71) Applicant: KONINKLIJKE PHILIPS N.V., Eindhoven (NL)

(72) Inventors: Rieko Verhagen, Eindhoven (NL); Bastiaan Wilhelmus Maria Moeskops, Eindhoven (NL); Mark Thomas Johnson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 954 days.

(21) Appl. No.: 14/396,767

(22) PCT Filed: Apr. 15, 2013

(86) PCT No.: PCT/IB2013/052976
§ 371 (c)(1),
(2) Date: Oct. 24, 2014

(87) PCT Pub. No.: WO2013/160798
PCT Pub. Date: Oct. 31, 2013

(65) Prior Publication Data
US 2015/0080866 A1   Mar. 19, 2015

(30) Foreign Application Priority Data

Apr. 27, 2012 (EP) .................................. 12165835

(51) Int. Cl.
*A61B 18/20* (2006.01)
*B26B 19/38* (2006.01)
(Continued)

(52) U.S. Cl.
CPC ............ *A61B 18/203* (2013.01); *A61B 18/20* (2013.01); *B26B 19/38* (2013.01);
(Continued)

(58) Field of Classification Search
CPC ........ A61B 18/203; A61B 2018/00476; A61B 2018/00452; A61B 2090/036; A61B 18/20; B26B 19/38
(Continued)

(56) References Cited

U.S. PATENT DOCUMENTS 5,533,266 A * 7/1996 Kelman ............... A61B 18/203
132/200
5,993,440 A * 11/1999 Ghassemi ............... B26B 19/00
30/41.5
(Continued)

FOREIGN PATENT DOCUMENTS

WO    9216338 A1    10/1992
WO    9533600 A1    12/1995
(Continued)

*Primary Examiner* — Christopher Koharski
*Assistant Examiner* — Pamela M. Bays

(57) ABSTRACT

A cutting element for a cutting head for a device for cutting hair is disclosed. A laser beam is directed across a cutting zone, in the cutting head, substantially parallel to a user's skin. The laser beam has an effective cutting region in which the laser beam is of a sufficient intensity to cut hair entering said region. The cutting element has a guard adjacent to the cutting zone to contact a user's skin and space the laser beam there from. The guard has a non-planar shape in a direction extending across the cutting zone so that it substantially follows the contours of an edge of the effective cutting region of the laser beam to reduce any variation in the distance between the edge of the effective cutting region and the user's skin across the length of the cutting zone.

15 Claims, 3 Drawing Sheets

(51) Int. Cl.
*A61B 18/00* (2006.01)
*A61B 90/00* (2016.01)

(52) U.S. Cl.
CPC ............... *A61B 2018/00452* (2013.01); *A61B 2018/00476* (2013.01); *A61B 2090/036* (2016.02)

(58) Field of Classification Search
USPC .......................................................... 606/9
See application file for complete search history.

(56) References Cited

U.S. PATENT DOCUMENTS

| | | |
|---|---|---|
| 2005/0273089 A1 | 12/2005 | Kreindel |
| 2015/0080866 A1 | 3/2015 | Verhagen |

FOREIGN PATENT DOCUMENTS

| | | |
|---|---|---|
| WO | 2008146789 A1 | 12/2008 |
| WO | 2011010246 A1 | 1/2011 |

* cited by examiner

DEVICE FOR CUTTING HAIR

This application is the U.S. National Phase application under 35 U.S.C. § 371 of International Application No. PCT/IB2013/052976, filed on Apr. 15, 2013, which claims the benefit of European Application No. 12165835.5 filed on Apr. 27, 2012. These applications are hereby incorporated by reference herein.

FIELD OF THE INVENTION

This invention relates to a device for cutting hair.

BACKGROUND OF THE INVENTION

It is known to provide a shaver or razor that relies on a laser for cutting hair rather than an arrangement of cutting blades. Shavers without blades have fewer moving parts and so wear is reduced, providing an advantage over mechanical shavers. Furthermore, the use of a laser can reduce skin irritation as there are no sharp objects that contact the skin surface. Laser shavers work by optical absorption in which hair exposed to a laser beam absorbs the energy of the beam, causing it to be vaporized and/or severed.

Shaving performance is typically measured by two criteria—closeness of shave and irritation of the skin. The cutting height is the distance between the surface of the skin and the point at which hairs are cut. A good performing shaver should minimize the cutting height and therefore minimize the remaining hair length by positioning the laser beam as close as possible to the skin. A good performing shaver should also minimize the variation in cutting height and therefore the remaining hair length should be uniform. However, positioning the laser beam close to the skin may cause more skin irritation if heat and energy from the laser is incident on the skin. It is necessary to protect the skin from contact with the laser beam to avoid damaging or irritating the skin being shaved. Hair trimmers or groomers are used to trim hair to a constant length, so although closeness is not a major performance factor, uniformity of remaining hair length is desirable.

Typically, to protect the skin from the laser and limit irritation, a comb is positioned between the laser beam and the skin to manipulate hair and limit contact between the skin and laser beam. However, this can be detrimental to the closeness of cut as it increases the distance between the skin surface and the laser beam.

It is known, for example from WO 95/33600, to provide a shaver that generates a laser beam that is positioned parallel to the skin and perpendicular to the stroke direction to cut hairs as the shaver is moved over the skin. However, Gaussian theory dictates that lasers have a natural intensity variation along their length. Beams will have a waist where the intensity and fluence are at a maximum and the beam width is at a minimum. Away from the waist, the beam width is larger and the intensity and fluence are decreased. This means that at the beam waist the energy of the laser beam is focused near to the centre of the beam, on a small area of a hair to be cut. However, away from the waist, the energy is more distributed through the beam width and therefore spread over a larger area of a hair to be cut. This variation in intensity may cause variations in the cutting height of a laser shaver with a laser beam parallel to the skin surface.

SUMMARY OF THE INVENTION

It is an object of this invention to provide a device for cutting hair that overcomes or substantially alleviates the problems described above.

It is known from U.S. Pat. No. 5,993,440 to provide a cutting head for a device for cutting hair that uses a laser beam, the laser beam having a longitudinal axis that extends across a cutting zone, said laser beam having an effective cutting region in which the laser beam is of a sufficient intensity to cut hair entering said region, the cutting head comprising a guard adjacent to said cutting zone to contact a user's skin and space the laser beam therefrom.

A cutting head according to the present invention is characterised in that the guard has a non-planar shape in a direction extending across the cutting zone so that it substantially follows a contour that extends across the cutting zone in the longitudinal direction of the laser beam, and which defines an edge (Y) of said effective cutting region of the laser beam to reduce any variation in the distance between said edge of the effective cutting region and the user's skin across the length of the cutting zone.

Shaping the guard to match or approximately match an edge of the effective cutting region of the laser beam improves the performance of the device over known shavers and trimmers because the cutting height variation caused by intensity variations in the laser beam is reduced. In this way, during use, the distance between the skin of a user and the effective cutting region in the laser beam will be substantially constant, meaning that the remaining hair length is more uniform. This enables hairs to be accurately and effectively cut to a more uniform length, as desired by the user.

The guard may be positioned relative to the edge of the effective cutting region to minimize the distance between the effective cutting region and a user's skin (5) across the length of the cutting.

This would be applicable if the hair cutting device were being used as a shaver, where the remaining hair length should be as short as possible. In other cases, such as for a hair trimming device, the guard may be spaced from the laser beam so that the remaining hair length is longer but uniformity is not affected.

In one embodiment, the guard comprises two planar portions angled with respect to each other and which meet at an apex, said apex being located between the ends of the cutting zone.

The two planar portions of the guard will cause the skin to deform as the cutting head is pressed against the skin during use, thereby reducing the cutting height of the device. The guard also limits the variation in cutting height across the cutting zone as the two planar portions are formed to approximately match the edge of the effective cutting region of the laser beam.

The apex may be located at a mid-point between the ends of the cutting zone. If the cutting laser beam is configured such that the effective cutting region has a high intensity waist located centrally in the cutting zone, then the guard should be shaped such that the apex is aligned with the waist to reduce the variation in distance between the user's skin and the edge of the effective cutting region during use.

The apex may be in an offset, non-central position, between the ends of the cutting zone.

If the cutting laser beam is configured such that the effective cutting region has a high intensity waist located non-centrally within the cutting zone, then the guard should be shaped such that the apex is aligned with the waist to reduce the variation in distance between the user's skin and the edge of the effective cutting region during use. In another embodiment, the guard is arcuate in shape to present a concave surface to the user's skin.

The curved guard more closely matches the curvature of the edge of the effective cutting region of the laser beam meaning that the cutting height is reduced and the uniformity of remaining hair length is greatly improved. The guard will cause the skin to deform against the concave surface of the guard, maintaining a substantially constant distance between the skin surface and the edge of the effective cutting region, thereby improving uniformity of the remaining hair length.

The guard may have a substantially Gaussian shape.

The Gaussian equations can be used to determine the shape of the edge of the effective cutting region and can therefore also be used to define a Gaussian shape for the guard. The shape of this guard would closely match the edge of the effective cutting region, improving the uniformity of the remaining hair length.

The cutting head may also comprise an optical system comprising a reflective element for directing the laser beam substantially parallel to the skin of a user, across the cutting zone, perpendicular to a direction of movement of the device across a user's skin.

Gaussian laser beams maintain their optical properties when reflected, allowing an optical system with reflectors to be used to manipulate the laser beam. The laser beam may be parallel to the skin and perpendicular to the stroke direction of the device to maximize the width of the cutting zone.

The optical system may comprise a first reflective element to direct the laser beam from the laser beam generator across the cutting zone.

The first reflective element means that the laser beam generator does not have to be positioned in line with the cutting laser beam axis, saving space and reducing the size of the cutting head assembly.

The optical system may also comprise a second reflective element positioned on an opposite side of the cutting zone to the first reflective element to direct the laser beam away from the cutting zone.

The laser beam can be directed away from the skin after cutting to avoid inadvertent heating of the cutting head assembly or damage to the skin.

The optical system may comprise a second reflective element configured to direct the laser beam back across the cutting zone, such that a second laser beam is present in the cutting zone for cutting hair.

Having multiple laser beams in the cutting zone will improve the performance of the shaver because there is less opportunity for hairs to pass through the cutting zone without being severed by at least one the laser beams. Therefore, adequate shaving or trimming performance may be achieved with fewer passes over the skin.

The first laser beam and the second laser beam may be configured to have differently shaped effective cutting regions.

Having differently shaped effective cutting regions means that the high intensity waists of the laser beams will be located in different positions. This will increase the amount of the cutting zone that is covered by a high intensity part of at least one laser beam, thereby improving hair severing performance.

The cutting head may comprise first and second guards adjacent to the first and second laser beams, to contact a user's skin and space each laser beam there from, wherein the first and second guards (36, 37) each have a non-planar shape in a direction extending across the cutting zone (8) to substantially follow the contours that extend across the cutting zone in the longitudinal direction of the laser beam and which defines an edge of each effective cutting region of the first and second laser beams (15, 29).

Multiple guards can be provided to maintain spacing between the multiple laser beams and the user's skin during use. Also, the guards will limit irritation caused to the skin and reduce the variation in cutting height across the cutting zone. Two guards are required if there are two laser beams in the cutting zone having differently shaped effective cutting regions.

The cutting head may comprise a plurality of cutting elements. A cutting head with a plurality of cutting elements would improve the cutting performance of the device because either multiple laser beams would pass over the same area or a larger area can be covered with a single pass.

According to another aspect of the invention, there is provided a device for cutting hair comprising a cutting head as described above.

BRIEF DESCRIPTION OF THE DRAWINGS

Embodiments of the invention will now be described, by way of example only, with reference to FIGS. 3 to 5 of the accompanying drawings, in which.

DETAILED DESCRIPTION OF THE EMBODIMENTS

Figure 1:
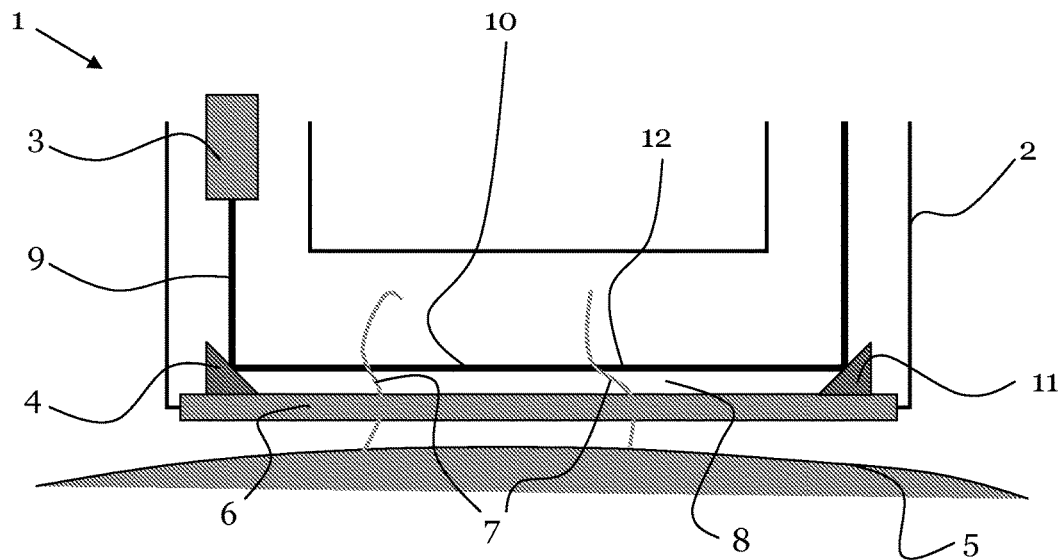
FIG. 1 shows a laser shaver cutting element, as is known in the art.

Referring to the drawings, FIG. 1 shows a schematic diagram of a laser shaver 1 cutting head that is known in the art. The laser shaver comprises a body 2, a diode 3 and first and second reflective elements 4, 11. Only the cutting head is shown, although this shaver also includes a handle that rigidly attaches to the cutting head to allow a user to hold and move the cutting head over the skin 5.

The cutting head comprises a guard 6 that manipulates hairs 7 into a cutting zone 8 as the shaver 1 is moved over the skin 5. The diode 3 is located on one side of the cutting head and emits a laser beam 9 towards the cutting zone 8. The first and second reflective elements 4, 11 are positioned to direct the beam 9 so that a cutting beam axis 12 is positioned across a cutting zone 8 that is adjacent to the guard 6 and then away from the cutting zone 8 back towards the handle. In this way, the hairs 7 are exposed to the cutting laser beam 10 as it passes through the cutting zone 8 and the hairs 7 are severed by optical absorption.

It is typical to use a diode that emits a Gaussian laser beam in applications of this type; the principle advantage of Gaussian lasers is that the beam characteristics are maintained when a beam is reflected. Gaussian beam theory dictates that the intensity distribution and width of a laser beam vary along the beam's longitudinal axis. So, if the cutting laser beam axis is parallel to the skin surface, the distance between the skin and the edge of an effective cutting region of the laser beam with sufficient energy and intensity to sever hair will also vary. In particular, the laser beam will have a high intensity region with a narrow waist located between the two reflective elements and lower intensity regions with maximum beam width at each reflective element. Within the high intensity region the energy of the laser beam is focused in a small area around the centre of the beam and within the lower intensity regions the beam energy is more distributed. Therefore, at the waist, the portion of the beam with sufficient energy to sever hair has a smaller beam width than at the lower intensity regions. However, the overall power of the laser beam can be selected such that the lower intensity regions have sufficient energy to sever hair. Gaussian equations and models can be used to determine the intensity, width, power and fluence of the laser beam at any distance from the main optical axis of the beam as well as the exact location of the high intensity waist.

The variation of beam width of a Gaussian beam is described in the following equation:

$$w(z) = w_0 \sqrt{\left[1 + M^2\left(\frac{z^2}{z_R^2}\right)\right]}$$

Wherein $w(z)$ is the beam radius at a distance z from the beam waist (focus), $w_0$ is the radius of the beam waist and $z_R$ is the Rayleigh range, while $M^2$ is the beam propagation factor which is a measure of beam quality. The Rayleigh range ($z_R$) of a laser beam is defined as the distance over which the beam surface area is doubled and is described by the following equation:

$$z_R = \frac{\pi \cdot w_0^2}{\lambda}$$

Where $\lambda$ is the wavelength of the laser beam.

The above equations can be used to create an expression of the shape of the edge of the envelope of the laser beam with sufficient energy and intensity to sever hair.

Figure 2:
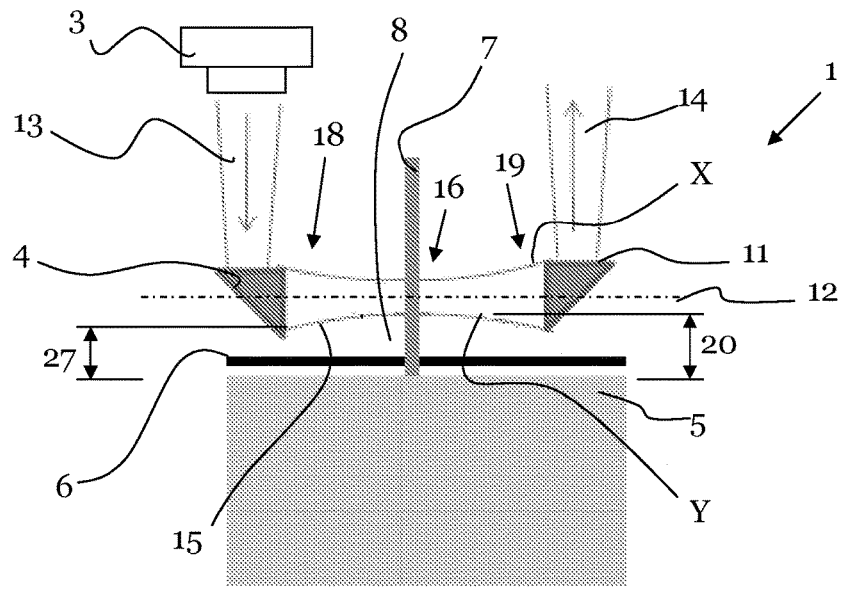
FIG. 2 shows a schematic diagram of a laser shaver cutting element, as is known in the art, with a planar guard.

FIG. 2 shows a schematic diagram of a laser shaver cutting head as is known in the art, with first and second reflective elements 4,11, in this case prismatic members. The first reflective element 4 reflects an input laser beam 13 across the cutting head to the second reflective member 11, which is positioned on the opposite side of the cutting head to reflect the laser beam back away from the cutting head. The laser beam between the first and second reflective elements 4,11 defines a cutting laser beam 15 within a cutting zone 8. The high intensity waist 16, or focus, is clearly shown equidistant between the first and second reflective elements 4,11 and on the optical axis 12 which runs substantially parallel to, and at a substantially constant distance from, the surface of the skin 5 during use. This view shows the laser shaver cutting head assembly 1 as it would look if it were moving towards the reader, across the skin 5.

The minimum energy required to sever hair can be determined by experiment or calculation and Gaussian beam theory can be used to define an effective cutting region within the cutting beam with sufficient intensity and energy to sever hair. Due to the Gaussian intensity variations along the length of the cutting beam 15, the effective cutting region will not incorporate the entire beam and will be shaped as shown by lines X and Y in FIG. 2, which represent the edges of the effective cutting region and therefore represent lines of intensity in the laser beam which are sufficient to cut hair.

The overall power of the cutting laser beam 15 can be selected such that the effective cutting region will extend into the end regions 18, 19 of the cutting laser beam despite the reduced intensity in these areas. This may result in the beam intensity and power in the waist region far exceeding that required to sever hair. The width of the part of the beam with sufficient intensity to sever hair in the regions 18, 19 away from the waist 16 means that cutting will occur at a greater distance from the optical axis 12 than at the narrow waist 16. For example, if it was known that 35% of the laser beams maximum intensity was required to sever hair then the effective cutting region X, Y would be bounded by the lines X and Y that represent the portion of the beam with at least 35% of the maximum beam intensity. The area within the lines X, Y will have more than 35% of the maximum beam intensity and the area outside of the lines X, Y will have less than 35% of the maximum beam intensity. The effective cutting region formed between the lines of constant intensity X, Y would be narrower at the waist 16 and wider at the ends 18,19, as shown in FIG. 2, because of the variation in intensity distribution along the longitudinal axis of the laser beam.

The shaver shown in FIG. 2 also comprises a planar guard 6 that manipulates hairs 7 into the cutting zone 8 and maintains a minimum distance between the skin surface 5 and the main optical axis 12 of the cutting laser beam 15. The guard 6 comprises a thin planar portion that presses against the skin surface 5 so that the distance from the skin 5 to the optical axis 12 of the laser beam 15 is controlled during use. The guard 6 also comprises a plurality of openings (not shown) that allow hairs 7 to protrude through the guard 6 and into the path of the cutting laser beam 15 where they are severed by optical absorption.

The varying width of the effective cutting region X, Y results in variations in the distance between the skin surface 5 and the height at which hairs 7 are severed—the cutting height. This remaining hair length will be longest if hair is severed by the narrow waist 16 and shortest if hair is severed by the end regions 18,19 of the cutting envelope X, Y; hair cut by the narrow waist 16 of the effective cutting region X, Y will remain longer after shaving than hairs cut by the end regions 18, 19 of the effective cutting region X, Y. This variation in cutting height across the cutting zone 8 is undesirable as it leads to non-uniformity in the remaining hair length and to achieve a more uniform shave will require more passes and therefore more time and irritation. Distance 20 on FIG. 2 represents the maximum cutting height, or remaining hair length, for hairs that are cut by the waist 16 of the effective cutting region X, Y and distance 27 represents the minimum cutting height, or remaining hair length, for hairs that are cut by the end regions 18, 19 of the cutting laser beam 15. As can be seen, there is a variation in cutting height across the cutting zone 8.

It is desirable to increase the uniformity of the remaining hair length without causing increased irritation to the skin by reducing the variation in cutting height caused by the intensity variation of the cutting laser beam 15. In the case of a shaver, it may also be desirable to minimize the cutting height and therefore the remaining hair length. The guard can be designed to manipulate the skin surface 5 to control the cutting height and the variation in cutting height, as will be described with reference to FIGS. 3 and 4.

Figure 3:
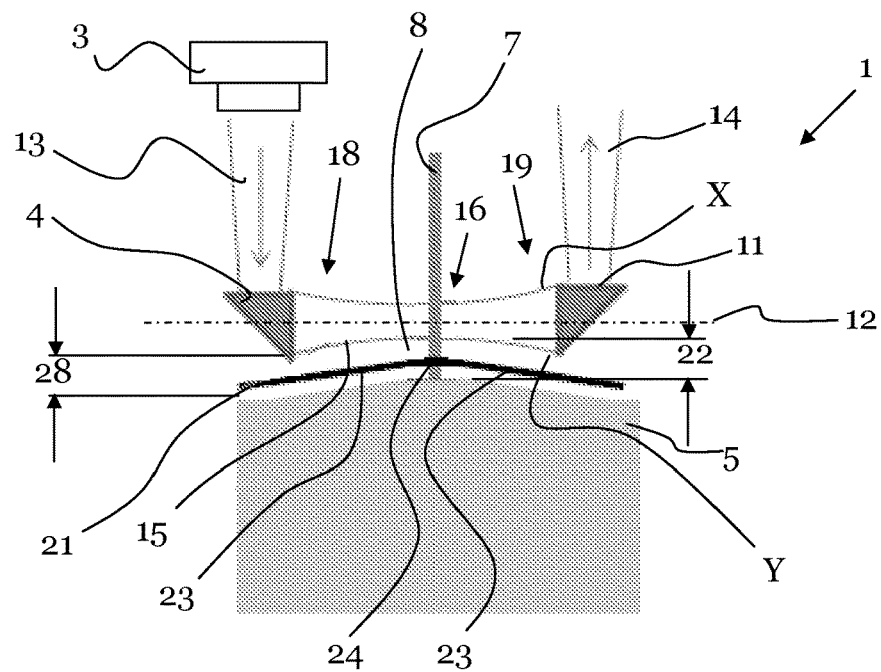
FIG. 3 shows a schematic diagram of a laser shaver cutting element with a guard.

FIG. 3 shows a schematic diagram of a cutting head 1 for a laser shaver with reflective elements 4,11 and a cutting laser beam 15 that can be defined by the Gaussian equations, as described with reference to FIG. 2. The diagram also shows an improved guard 21 that manipulates the surface of the skin 5 to control the cutting height when the shaver is in use, as shown. A hair 7 is shown protruding from the skin 5 through the guard 21 and into the cutting zone 8, where it will be severed by the cutting laser beam 15 at the boundary line Y—the edge of the effective cutting region X, Y with sufficient intensity to sever hair.

In this embodiment, the guard 21 has two planar inclined portions 23 angled with respect to each other that are designed to substantially follow the contours of curvature of an edge Y of the effective cutting region X, Y. As shown in FIG. 3, the guard 21 has an edge, along which the inclined portions 23 are joined, defining an apex 24 that is aligned with the waist 16 of the effective cutting region X, Y, in the middle of the cutting zone 8. The inclined portions 23 incline away from the apex 24 so that the distance from the main optical axis 12 of the laser beam 15 to the bottom surface of the guard 21 increases as the laser beam moves away from the waist 16 of the effective cutting region X, Y towards the first and second reflective elements 4,11. In this way, the shape of the guard 21 is representative of the edge Y of the effective cutting region X, Y.

Similarly to the planar guard 6 described with reference to FIG. 2, the inclined guard 21 has at least one, optionally a plurality of openings (not shown) that allow hairs 7 to protrude through and into the cutting zone 8 where they are severed. During use, when the user applies pressure on the shaver, the inclined portions 23 will cause the skin 5 to deform into the region between the inclined portions 23, as shown. The guard 21 therefore maintains a substantially constant spacing between the skin surface 5 and the edge Y of the effective cutting region X, Y during use, reducing variation in cutting height. Distance 22 shows the maximum cutting height which is reduced compared to the maximum cutting height 20 of the laser shaver described with reference to FIG. 2. Furthermore, the difference between the maximum cutting height 22 and the minimum cutting height 28 is reduced, improving uniformity of cut across the cutting zone 8. The guard 21 still maintains the required separation between the skin 5 and the laser beam 15 to protect the skin against further irritation.

Figure 4:
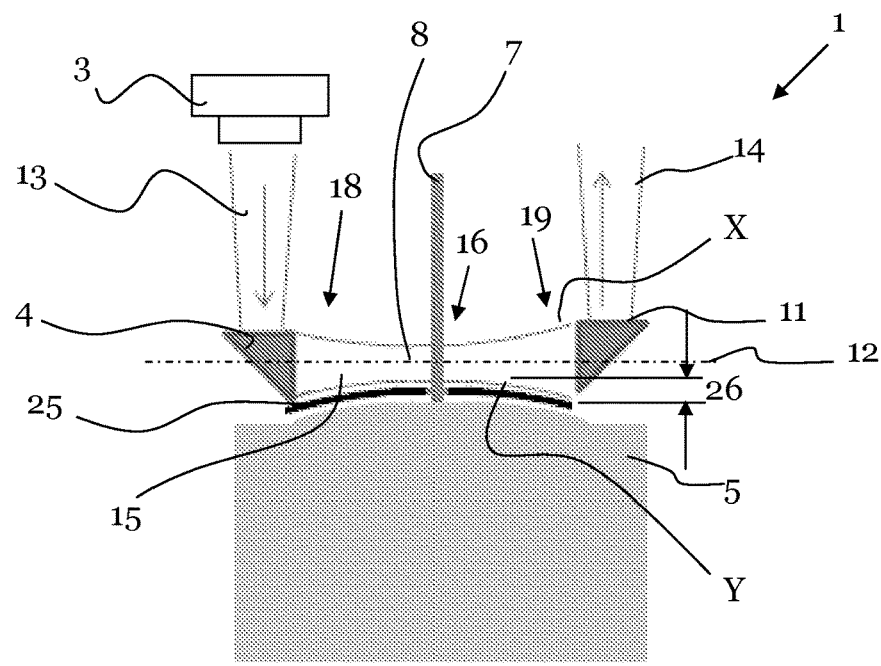
FIG. 4 shows a schematic diagram of a laser shaver cutting element with a guard.

FIG. 4 shows another embodiment of the laser shaver element 1 with a cutting laser beam 15 as described with reference to FIGS. 2 and 3. This embodiment also comprises a guard 25 for maintaining spacing between the effective cutting region X, Y and the surface of the skin 5 and, in this embodiment, the guard 25 is curved to match the curvature of the edge Y of the effective cutting region X, Y. Essentially, the guard 25 has a Gaussian profile so that the profile of the guard 25 matches the curvature of the edge Y of the effective cutting region X, Y. As before, the guard 25 will have at least one, optionally a plurality of openings (not shown), which allow hair 7 to protrude through into the cutting zone 8 where they are severed by optical absorption. During use, when the concave surface of the guard 25 is pressed against the skin 5 the skin will deform into the curved area of the guard 25 and the cutting height 26 will be substantially constant across the cutting zone 8. In this way, the remaining hair length may be further reduced and more consistent in comparison to the arrangements described with reference to FIGS. 2 and 3. The curvature of the guard 25 can be matched to the curvature of the effective cutting region X, Y to achieve optimum results. The guard 25 still acts as a protective boundary between the laser beam 15 and the skin 5 so skin irritation will not be worsened.

The embodiments described with reference to FIGS. 3 and 4 describe the high intensity waist 16 of the laser beam 15 being located centrally, equidistant between the ends of the cutting zone 8. However, it will be appreciated that the focus of the laser beam 15 may be adjusted using optical lenses so that the effective cutting region X, Y is asymmetrical and the waist 16 is offset from the centre of the cutting zone 8. This would require the guard 21, 25 to be asymmetrically shaped to match the asymmetrical shape of the effective cutting region X, Y. Therefore, for the embodiment described with reference to FIG. 3, the apex 24 would be offset from the centre of the cutting zone 8 and the two planar portions 23 would be different sizes. For the embodiment described with reference to FIG. 4, the arcuate guard 25 would be asymmetrical with the point of the guard closest to the cutting axis 12 being offset from the centre of the cutting zone 8.

Figure 5:
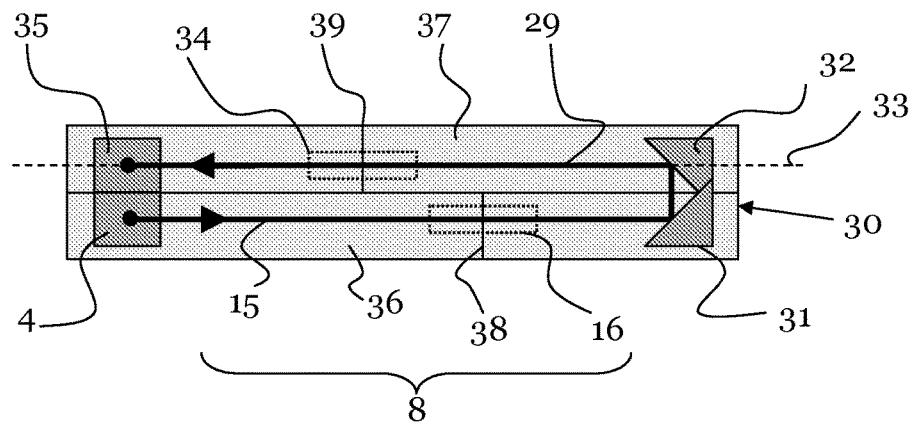
FIG. 5 shows a top view schematic diagram of a laser shaver cutting element with two cutting beams; and, FIG. 6 shows a schematic diagram of a laser shaver cutting head with multiple cutting elements.

FIG. 5 shows a top view schematic diagram of another embodiment of the invention. The lines representing the laser beams 15, 29 are only representative of the direction of the laser beams and do not show the Gaussian intensity distributions which would be present. FIG. 5 shows the first reflective element 4 which reflects the first cutting laser beam 15 across the cutting zone 8 as before. The high intensity waist 16 is located in the dotted area and is shown in an offset, non-central position within the cutting zone 8. In this embodiment, the second reflective element 30 comprises two portions 31, 32 configured to reflect the laser beam 15 back across the cutting zone 8, to create a second cutting beam 29 that passes through the cutting zone 8, therefore improving the cutting performance of the shaver. The cutting beam 15 may be reflected along a second optical axis 33 in the cutting zone 8, such that there are two parallel adjacent cutting beams 15, 29 across the cutting zone 8. Alternatively, the second cutting beam may be at an angle to the first cutting beam.

The second laser beam 29 also has a high intensity waist 34 and this second waist 34 is also in an offset, non-central position within the cutting zone 8. The first and second laser beams 15, 29 are focused such that the first waist 16 and the second waist 34 are not aligned with each other. In this way, the two high intensity waist regions 16, 34 can be positioned such that more of the cutting zone is covered by a high intensity region of at least one of the laser beams 15, 29, thereby improving cutting performance. It will be appreciated that the arrangement of the waists described above is only an example, and the waists may be aligned, separated or overlapping, depending on the requirements of the hair cutting device. The offset position of the waist regions 16, 34 can be achieved by altering the focus of the laser beams 15, 29 using one or several optical lenses (not shown). A third reflective element 35 is positioned to reflect the second laser beam 29 away from the cutting zone 8 and away from the skin of the user.

To space the laser beams 15, 19 from the skin and to improve the uniformity of cutting height across the cutting zone 8, two adjacent asymmetrical guards 36, 37 are provided that substantially follow the shape of the effective cutting regions of the laser beams 15, 29 with offset high intensity waists 16, 34. Each laser beam 15, 29 with a differently positioned waist will require a different guard. Therefore, as shown in FIG. 5, two adjacent guards 36, 37 are provided, each with two planar inclined portions joined at an apex, similar to the guard described with reference to FIG. 3. However, in this embodiment, each guard 36, 37 has an offset apex 38, 39 that is aligned with the waist 16, 34 of the laser beam 15, 29 that it is adjacent to. As described with reference to FIGS. 3 and 4, the shape of each guard 36, 37 is designed to follow the contours of the edge of the effective cutting region of each laser beam, thereby reducing the variation in cutting height across the cutting zone.

In an alternative embodiment, which is not shown in the drawings, each guard 36, 37 may have an arcuate shape that follows the shape of the effective cutting region of each laser beam 15, 29, as described with reference to FIG. 4. Arcuate guards will more closely follow the contours of the edge of the effective cutting regions of the laser beams 15, 29 and therefore reduce cutting height variation across the cutting zone 8. The shape of each guard will be asymmetrical to match the shape of the asymmetrical effective cutting region with an offset waist.

Optionally, additional subsequent reflective elements (not shown) may be used to reflect the laser beam back across the cutting zone 8 multiple times, allowing the beam to pass for third, fourth and fifth times across the cutting zone. This will improve the cutting performance of the shaver still further. Each additional laser beam with a different position waist would require an additional, appropriately shaped guard.

Figure 6:
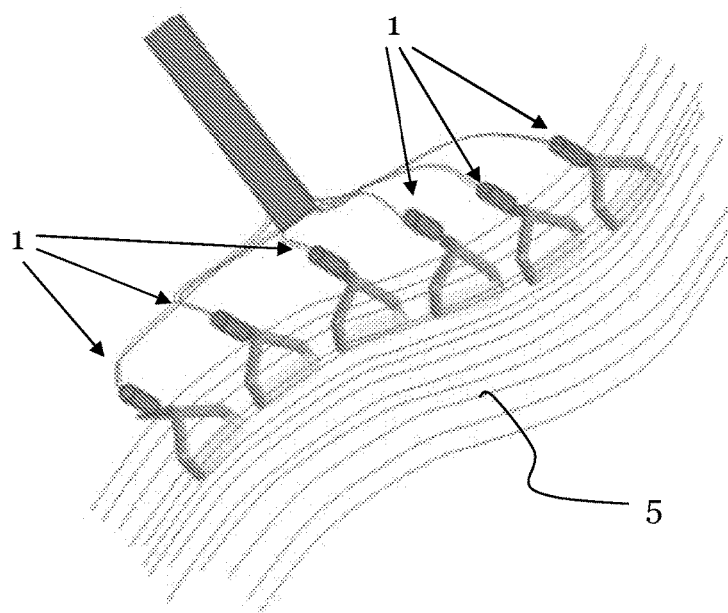

FIG. 6 shows a cutting head for a shaver with a plurality of laser cutting elements 1 in the same cutting head arranged adjacent to each other within a shaver that can be moved over the skin 5 to simultaneously shave a larger area. Each laser cutting element 1 may be independently moveable with respect to the handle of the shaver, axially and/or rotationally, so that the cutting elements 1 can move to follow the contours of the skin 5.

The shaving device described with reference to FIGS. 3 to 6 relates to shaving the skin to achieve a minimum remaining hair length as well as improved uniformity of remaining hair length. To achieve the minimum remaining hair length possible, the guard is positioned immediately adjacent to the edge of the effective cutting region. However, the device for cutting hair defined in the claims may alternatively be used for trimming hair to a controlled length that is not necessarily as short as possible, as is the case with a hair trimming or grooming device. To achieve this, the guard would be positioned further from the cutting laser beam so that the cutting length is increased, but remains uniform.

It will be appreciated that the cutting head described with reference to FIG. 6 may be a separate cutting head unit that is attachable to a shaver handle. The laser beam generator may be located either in the handle or in the detachable cutting head. Alternatively, a cutting head with multiple cutting elements may be integrated with a shaver handle as one product.

It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived there from.

Other modifications and variations falling within the scope of the claims hereinafter will be evident to those skilled in the art.

The invention claimed is:

1. A cutting head for a device for cutting hair that uses a laser beam, the laser beam having a longitudinal axis that extends in a first direction across a cutting zone along a user's skin during use of the device, the laser beam having an effective cutting region in which the laser beam is of a sufficient intensity to cut hair entering the region, the cutting head comprising:
a guard adjacent to the cutting zone, that during use of the device, contacts the user's skin so that the user's skin conforms to the shape of the guard and spaces the laser beam from the user's skin,
wherein the guard has a non-planar shape that extends in the first direction across the cutting zone so that the non-planar shape substantially follows a contour that extends in the first direction across the cutting zone, and wherein the contour defines an edge of the effective cutting region of the laser beam such that, during use of the device, any variation in a distance between the edge of the effective cutting region and the user's skin, which is in conformity with the shape of the guard, across a length of the cutting zone is reduced.

2. The cutting head of claim 1, wherein the guard is positioned relative to the edge of the effective cutting region such that, during use of the device, the distance between the edge of the effective cutting region and a user's skin is minimized across the length of the cutting zone.

3. The cutting head of claim 1, wherein the guard comprises two planar portions angled with respect to each other and which meet at an apex, the apex being located between the ends of the cutting zone.

4. The cutting head of claim 3, wherein the apex is located at a mid-point between the ends of the cutting zone.

5. The cutting head of claim 3, wherein the apex is in an offset, non-central position, between the ends of the cutting zone.

6. The cutting head of claim 1, wherein the guard is arcuate in shape to present a concave surface to a user's skin during use of the device.

7. The cutting head of claim 1, wherein the guard has a substantially Gaussian shape.

8. The cutting head of any preceding claim, further comprising an optical system coupled to the cutting head for directing the laser beam substantially parallel to the skin of a user, across the cutting zone, perpendicular to a direction of movement of a shaver, across a user's skin when the shaver is in use.

9. The cutting head of claim 8, wherein the optical system comprises a first reflective element to direct the laser beam from a laser beam generator across the cutting zone.

10. The cutting head of claim 9, wherein the optical system further comprises a second reflective element positioned on an opposite side of the cutting zone to the first reflective element to direct the laser beam away from the cutting zone.

11. The cutting head of claim 9, wherein the laser beam directed across the cutting zone by the first reflective element is a first laser beam, and wherein the optical system comprises a second reflective element configured to direct the first laser beam back across the cutting zone, such that a second laser beam is present in the cutting zone for cutting hair.

12. The cutting head of claim 11, wherein the first laser beam and the second laser beam are configured to have differently shaped effective cutting regions.

13. The cutting head of claim 12, wherein the guard comprises first and second guards adjacent to the first and second laser beams that during use of the device, contact a user's skin so that the user's skin conforms to the shape of the first and second guards and spaces each laser beam from the user's skin, wherein the first and second guards each have a non-planar shape in the first direction extending across the cutting zone to substantially follow contours that extend in the first direction across the cutting zone of each asymmetrically shaped effective cutting region of the first and second laser beams.

14. The cutting head according to claim 1, comprising a plurality of cutting elements.

15. A device for cutting hair, comprising a cutting head according to claim 1.

* * * * *